US008206694B2

(12) United States Patent
Chang et al.

(10) Patent No.: US 8,206,694 B2
(45) Date of Patent: Jun. 26, 2012

(54) ANTI-DANDRUFF HAIR CONDITIONING COMPOSITIONS

(75) Inventors: Wanlin Chang, Bangkok (TH); Kanjana Phattarasakul, Bangkok (TH); Busaraporn Samran, Bangkok (TH); Jie-bing Zhu, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 410 days.

(21) Appl. No.: 12/309,119

(22) PCT Filed: Jul. 2, 2007

(86) PCT No.: PCT/EP2007/056643
§ 371 (c)(1),
(2), (4) Date: May 11, 2009

(87) PCT Pub. No.: WO2008/003677
PCT Pub. Date: Jan. 10, 2008

(65) Prior Publication Data
US 2010/0016271 A1    Jan. 21, 2010

(30) Foreign Application Priority Data
Jul. 7, 2006   (EP) .................................... 06253590

(51) Int. Cl.
*A61Q 5/00*   (2006.01)
*A61Q 5/12*   (2006.01)
(52) U.S. Cl. .................................... 424/70.28; 424/70.1
(58) Field of Classification Search ........................ None
See application file for complete search history.

(56) References Cited

U.S. PATENT DOCUMENTS

| 5,659,047 A | 8/1997 | Vanlerberghe et al. ..... 548/313.7 |
| 2002/0155086 A1 | 10/2002 | Verdun et al. .................. 424/74 |
| 2002/0168327 A1 | 11/2002 | Bailey |
| 2003/0003070 A1 | 1/2003 | Eggers |
| 2003/0228272 A1 | 12/2003 | Amjad |
| 2007/0104671 A1 | 5/2007 | Fack |

FOREIGN PATENT DOCUMENTS

| DE | 3309765 A1 | 9/1984 |
| DE | 102005003949 A1 | 8/2005 |
| EP | 074 819 | 3/1983 |
| EP | 0074819 A2 | 3/1983 |
| EP | 0338850 A2 | 10/1989 |
| EP | 0813859 A2 | 12/1997 |
| EP | 1 520 575 | 4/2005 |
| EP | 1782791 A1 | 5/2007 |
| FR | 2 677 982 | 12/1992 |
| JP | 2004143097 A | 5/2004 |
| JP | 2006225307 A | 8/2006 |
| WO | WO0135912 A1 | 5/2001 |
| WO | WO0143706 A1 | 6/2001 |
| WO | 02/067880 | 9/2002 |
| WO | WO02067880 A1 | 9/2002 |
| WO | WO03007901 A1 | 1/2003 |
| WO | WO2004035015 A1 | 4/2004 |

OTHER PUBLICATIONS

EP Search Report in EP application EP 06 25 3590.
PCT Search Report in PCT application PCT/EP2007/056643.
Abstract of FR 2 846 231—published Apr. 30, 2004.
Abstract of DE 41 34 137—published Apr. 22, 1993.
Mintel, Intensive mask, Mintel GNPD Intensive mask, Feb. 2004, 1-2.
*Helianthus annuus* Seed Extract, Kosmetikanalyse pp. 1-2, 1-2.
Cetrimonium Chloride, On-Line INFOBASE Personal Care Products Council, 1-2.
Apricot oil, Wikipedia, the free encyclopedia, 1.
Cetearyl Alcohol, On-Line INFOBASE Personal Care Products Council, 1.
Dihydroxypropyl PEG-5 Linoleammonium Chloride, On-Line INFOBASE Personal Care Products Council, 1-2.
O'Lenick, Jr., Triglycerides—Important Cosmetic Raw Materials, Siltech LLC, 1-3.
Wikipedia, Sunflower seed, Wikipedia, the free encyclopedia, 1-5.
Mintel, Anti Dandruff Shampoo, Mintel GNPD Anti Dandruff Shampoo, Mar. 2006, 1-2.
Mintel, Balance Total Headcare Shampoo, Mintel GNPD Balance Total Headcare Shampoo, Apr. 2005, 45-46.
Mintel, Clear Purify Total Headcare Shampoo, Mintel GNPD Clear Purify Total Headcare Shampoo, Jan. 2005, 1-2.
Intensive Mask, Mintel GNPD Intensive Mask, Feb. 2004, 579-580.
Extra Rich-Nutrition Masque, Mintel GNPD Extra Rich-Nutrition, Aug. 2004, 463-464.
Hair Fall Defense Shampoo, Mintel GNPD Hair Fall Defense, Jun. 2006, 3-4.
Anti Dandruff Shampoo, Mintel GNPD Anti Dandruff Shampoo, Mar. 2006, 1-2.
Hairfall Defense Shampoo, Mintel GNPD Hairfall Defense Shampoo, Sep. 2005, 27-28.
Balance Total Headcare Shampoo, Mintel GNPD Balance Total Headcare, Apr. 2005, 45-46.
Clear Purify Total Headcare Shampoo, Mintel GNPD Clear Purify Total Headcare, Jan. 2005, 49-50.
Total Headcare Active Shampoo, Mintel GNPD Total Headcare Active, Nov. 2004, 55-56.
Total Headcare Shampoo, Mintel GNPD Total Headcare Shampoo, Sep. 2004, 59-60.
Ikill Etki Shampoo, Mintel GNPD Ikill Etki Shampoo, Jan. 2003, 73-74.
Herbal Care Conditioner, Mintel GNPD Herbal Care Conditioner, Jul. 2001, 77. Summer Blonde Range—Shampoo, Mintel GNPD Summer Blond Range—Shampoo, Jun. 2004, 65-66.
Long & Strong Nutrient Conditioner, Mintel GNPD Long & Strong Nutrient, Jul. 2005, 33-34.
Purify Scalp & Hair Conditioner, Mintel GNPD Purify Scalp & Hair, Jul. 2005, 35.
L'Oreal, EP2046453 Notice of Opposition—L'Oreal, Notice of Opposiiton—L'Oreal 2011, Dec. 29, 2011.
L'Oreal, L'Oreal Opposition Letter, L'Oreal Opposition Letter, Nov. 15, 2011, 1-5.

(Continued)

*Primary Examiner* — Jyothsna Venkat
(74) *Attorney, Agent, or Firm* — Ronald A. Koatz

(57) ABSTRACT

A hair conditioning composition comprising a cationic surfactant, triglyceride oil, and an anti dandruff agent.

1 Claim, No Drawings

OTHER PUBLICATIONS

L'Oreal, L'Oreal Opposiiton Letter—Translation, L'Oreal Opposiiton Letter—Translation, Nov. 15, 2011, 1-5.
Beiersdorf, Beiersdorf Notice of Opposition, Beiersdorf Notice of Opposition, Dec. 29, 2011, 1-2.
Beiersdorf, Beiersdorf Opposiiton Letter, Beiersdorf Opposiiton Letter, Nov. 2, 2011, 1-18.
Beiersdorf, Beiersdorf Opposition Letter—Translation, Beiersdorf Opposition Letter—Translation, Nov. 2, 2011, 1-7.
Henkel, Henkel Notice of Opposition, Henkel Notice of Opposition, Dec. 29, 2011, 1.
Henkel, Henkel Opposition Letter, Henkel Opposition Letter, Nov. 16, 2011, 1-12.
Henkel, Henkel Opposiiton Letter—Translation, Henkel Opposiiton Letter—Translation, Nov. 16, 2011, 1-18.
P&G, P&G Notice of Opposition, P&G Notice of Opposition, Dec. 29, 2011, 1-2.
P&G, P&G Opposition Letter, P&G Opposition Letter, Feb. 16, 2011, 1-9.
Kao, Kao Notice of Opposition, Kao Notice of Opposition, Dec. 29, 2011, 1-2.
Kao, Kao Opposition Letter, Kao Opposition Letter, Feb. 16, 2011, 1-14.
Extra Rich Nutrition Masque Reparateur, Mintel GNPD Extra Rich Nutrition Masque Reparateur, 2004, 1-3.
Hair Fall Defense Shampoo, Mintel GNPD Hair Fall Defense Shampoo 2006 pp. 1-3—Translation, 2006, 1-3.
Hairfall Defense Shampoo, Mintel GNPD Hairfall Defense Shampoo—Translation, Sep. 2005, 1-2.
Herbal Care Conditioner, Mintel GNPD Herbal Care Conditioner D3—Translation, Jul. 2001, 1-2.
Ikili Etki2 Shampoo, Mintel GNPD Ikili Etki2 Shampoo—Translation, Jan. 2003, 1-2.
Long & Strong Nutrient Conditioner, Mintel GNPD Long & Strong Nutrient Conditioner—Translation, Jul. 2005, 1-2.
Purify Scalp & Hair Conditioner, Mintel GNPD Purify Scalp & Hair Conditioner—Translation, Jul 2005, 1-2.
Summer Blonder Range—Shampoo, Mintel GNPD Summer Blonder Range—Shampoo—Translation, Jun. 2004, 1-3.
Total Headcare Active Shampoo, Mintel GNPD Total Headcare Active Shampoo—Translation, Nov. 2004, 1-2.
Total Headcare Shampoo, Mintel GNPD Total Headcare Shampoo—Translation, Sep. 2004, 1-2.
Fiebig, Composition of Important Edible Oils and Fats of Vegetable, Citation D13 pp. 1-2 Translation, 1-2.
Mintel, 2 in 1 Shampoo & Conditioner, Mintel GNPD 2 in 1 Shampoo, Aug. 2005, 1-4.
Mintel, 2 in 1 Shampoo & Conditioner, Mintel GNPD 2 in 1 Shampoo Conditioner, Aug. 2005, 1-2.
Mintel, Anti Dandruff Shampoo, Mintel GNPD Anti Dandruff Shampoo, Mar. 2006, 1-3.
Mintel, Anti Dandruff Shampoo, Mintel GNPD Anti Dandruff Shampoo, Mar. 2006, 1.
Mintel, CC7 Clinical Care Shampoo, Mintel CC7 Clinical Care Shampoo 2001 pp. 1-2 Translation, Feb. 2001, 1-2.
Mintel, CC7 Clinical Care Shampoo, Mintel GNPD CC7 Clinical Care Shampoo, Feb. 2001, 1.
Fiebig, Composition of Important Edible Oils and Fats, Henkel Citation D13, 1-3.
Kao, Novid Hair Conditioner, Kao Citation D2 Novid Hair Conditioner, Mar. 2002, 1-2.
Kao, Novid Hair Conditioner, Kao Citation D2 Novid Hair Conditioner, Mar. 2002, 1.
Mintel, Hairfall Defense Shampoo, Mintel GNPD Hairfall Defense Shampoo Translation, Sep. 2005, 1-2.
Mintel, Hairfall Defense Shampoo, Mintel GNPD Hairfall Defense Shampoo, Sep. 2005, 1-2.
Mintel, Intensive mask, Mintel GNPD Intensive mask Translation, Feb. 2004, 1-3.

ANTI-DANDRUFF HAIR CONDITIONING COMPOSITIONS

FIELD OF THE INVENTION

The present invention relates to hair conditioning compositions which comprise an antidandruff agent.

BACKGROUND TO THE INVENTION AND PRIOR ART

There is a need for effective compositions for the treatment of dandruff. One way of solving this problem is to prepare compositions that give better deposition of an antidandruff agent onto the hair and/or the scalp.

The present invention is based on the surprising finding that conditioning formulations can be formulated that give excellent deposition of antidandruff agents.

SUMMARY OF THE INVENTION

The invention provides a hair conditioning composition comprising a hair conditioning composition comprising a cationic surfactant, triglyceride oil and an anti dandruff agent.

The invention also provides a method of mitigating dandruff by applying to the scalp to the scalp a composition as described above.

DETAILED DESCRIPTION OF THE INVENTION

Antidandruff Agent

Compositions of the invention comprise an anti-dandruff agent. Preferred antidandruff agents include zinc pyrithione, octopirox, climbazole and ketoconazole.

Preferably, the anti-dandruff agent is in solution in the composition. The anti-dandruff agent is therefore preferably soluble in the composition of the invention at 25 degrees C. Most preferably, the anti-dandruff agent is climbazole (1-imidazolyl-1-(4-chlorophenoxy)-3,3-dimethylbutan-2-one).

The anti-dandruff agent may be a single anti-dandruff compound or a mixture of different anti-dandruff compounds.

Preferably, the anti-dandruff agent is present in the composition in an amount of from 0.1 to 5% by weight, more preferably from 0.1 to 2% by weight.

Triglyceride Oil

The hair conditioning composition of the invention comprises a triglyceride oil, preferred oils include avocado oil, olive oil, corn oil, rape seed oil, sesame oil, wheat germ oil, castor oil, linseed oil, sunflower oil, cottonseed oil, soybean oil, peanut oil, and mixtures thereof. Particularly preferred is sunflower oil.

The level of triglyceride oil is preferably from 0.1 to 10 wt % of the total composition, more preferably from 0.5 to 5 wt %, most preferably from 1 to 3 wt %.

The weight ratio of antidandruff agent to sunflower oil is preferably from 1:4 to 4:1, more preferably from 1:3 to 2:1, most preferably from 1:1 to 1:3.

Cationic Surfactant

Compositions according to the invention comprise one or more cationic surfactants which are cosmetically acceptable and suitable for topical application to the hair.

Suitable cationic surfactants for use in compositions of the invention contain amino or quaternary ammonium hydrophilic moieties which are positively charged when dissolved in the composition.

Suitable quaternary ammonium cationic surfactants correspond to the following general formula (I):

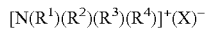

$$[N(R^1)(R^2)(R^3)(R^4)]^+(X)^- \quad \text{(I)}$$

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

In a suitable class of cationic surfactant of general formula (I), $R^1$ and $R^2$ are each independently selected from $C_{16}$ to $C_{22}$ hydrocarbyl chains comprising at least one ester linkage in both $R^1$ and $R^2$, and $R^3$ and $R^4$ are each independently selected from $CH_3$ and $CH_2CH_2OH$.

In another suitable class of cationic surfactant of general formula (I), $R^1$ and $R^2$ are each independently selected from $C_{16}$ to $C_{22}$ saturated or unsaturated, preferably saturated, chains, and $R^3$ and $R^4$ are each independently selected from $CH_3$ and $CH_2CH_2OH$, preferably $CH_3$.

In a preferred class of cationic surfactant of general formula (I), $R^1$ is a $C_{16}$ to $C_{22}$ alkyl chain and $R^2$, $R^3$ and $R^4$ are each independently selected from $CH_3$ and $CH_2CH_2OH$, preferably $CH_3$.

Specific examples of suitable quaternary ammonium cationic surfactants of general formula (I) are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate. Particularly preferred is behenyltrimethylammonium chloride (BTAC)

Mixtures of any of the foregoing materials may also be suitable.

Salts of primary, secondary, and tertiary fatty amines are also suitable cationic surfactants for use in the invention. The alkyl groups of such amines preferably have from about 12 to about 22 carbon atoms, and can be substituted or unsubstituted. These amines are typically used in combination with an acid to provide the cationic species.

A preferred class of amine corresponds to the following general formula (II):

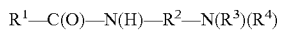

$$R^1—C(O)—N(H)—R^2—N(R^3)(R^4) \quad \text{(II)}$$

in which $R^1$ is a fatty acid chain containing from 12 to 22 carbon atoms, $R^2$ is an alkylene group containing from one to four carbon atoms, and $R^3$ and $R^4$ are, independently, an alkyl group having from one to four carbon atoms.

Specific examples of suitable materials of general formula (II) are stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

Particularly preferred is stearamidopropyldimethylamine.

Mixtures of any of the foregoing materials may also be suitable.

The acid used to provide the cationic species can be any organic acid or mineral acid of sufficient acid strength to neutralise a free amine nitrogen. Such acids include hydrochloric acid, sulphuric acid, nitric acid, phosphoric acid, lactic acid, citric acid, tartaric acid, acetic acid, gluconic acid, glycolic acid and propionic acid, or combinations thereof. In general, a sufficient amount of acid is added to neutralise the amidoamine compound and to adjust the final pH of the composition to within a range of from about 2.5 to about 6, preferably in a pH range of from about 3 to about 5. The molar ratio of protonatable amine groups to $H^+$ from the acid is preferably from about 1:0.3 to 1:1.2, and more preferably from about 1:0.5 to about 1:1.1.

Mixtures of any of the above-described cationic surfactants may also be suitable.

In the composition of the invention, the level of cationic surfactant preferably ranges from 0.1 to 10%, more preferably 0.2 to 5%, most preferably 0.25 to 4% by total weight of cationic surfactant based on the total weight of the composition.

It is preferred if the weight ratio of cationic surfactant to antidandruff agent is in the ratio of 4:1 to 1:4, preferably 1:2 to 2:1

Fatty Material

Compositions of the invention may comprise a fatty material. The fatty material, together with the cationic surfactant and an aqueous carrier, forms a lamellar gel phase which is suitable for providing various hair conditioning attributes.

By "fatty material" is meant a compound having the general formula R—X, wherein R is an aliphatic carbon chain and X is a functional group (e.g. alcohol, acid, or derivative).

R is preferably a fully saturated aliphatic carbon chain comprising from 8 to 30 carbon atoms, more preferably from 16 to 22 carbon atoms.

X is preferably an alcohol group.

Most preferably, the fatty material is selected from cetyl alcohol, stearyl alcohol, behenyl alcohol, and mixtures thereof.

The level of fatty material in conditioners of the invention suitably ranges from 0.01 to 15%, preferably from 0.1 to 10%, and more preferably from 0.1 to 5% by total weight fatty material based on the total weight of the composition.

The weight ratio of cationic surfactant to fatty material is suitably from 10:1 to 1:10, preferably from 4:1 to 1:8, more preferably from 1:1 to 1:7.

Aqueous Carrier

The conditioning composition of the present invention preferably comprises an aqueous carrier.

Suitable aqueous carriers are water and water solutions of lower alkyl alcohols and polyhydric alcohols.

Examples of suitable lower alkyl alcohols are monohydric alcohols having 1 to 6 carbons, preferably ethanol and isopropanol.

Examples of suitable polyhydric alcohols are propylene glycol, hexylene glycol, glycerin, and propanediol.

Preferably, the aqueous carrier is substantially water.

Generally, compositions according to the invention comprise at least 60%, preferably at least 65%, more preferably at least 70% water by weight based on the total weight of the composition.

Further Conditioning Agents

Compositions of the invention may comprise further conditioning agents to optimise wet and dry conditioning benefits.

Particularly preferred further conditioning agents are silicone emulsions.

Suitable silicone emulsions include those formed from silicones such as polydiorganosiloxanes, in particular polydimethylsiloxanes which have the CTFA designation dimethicone, polydimethyl siloxanes having hydroxyl end groups which have the CTFA designation dimethiconol, and aminofunctional polydimethyl siloxanes which have the CTFA designation amodimethicone.

Mixtures of any of the above described silicone emulsions may also be used.

Silicone will generally be present in a composition of the invention at levels of from 0.05 to 10%, preferably 0.05 to 5%, more preferably from 0.5 to 2% by total weight of silicone based on the total weight of the composition.

Other Optional Ingredients

Compositions according to the invention may also incorporate other cosmetically suitable ingredients, preferably at a level of 2% by weight or less. Suitable ingredients include: preservatives, colouring agents, chelating agents, antioxidants, fragrances, cationic conditioning polymers, styling ingredients, sunscreens, proteins and hydrolysed proteins.

Use

The compositions of the invention may be used by applying them to wet hair, typically hair which has been shampooed and then rinsed with water.

Generally, the composition is applied to the hair and then worked through the hair. Preferably the composition is then left to penetrate the hair for a period of about one to three minutes before rinsing it from the hair with water.

The invention will now be further described by reference to the following Examples. In the Examples, all percentages are by weight based on total weight, unless otherwise specified. Examples according to the invention are denoted by a number, whereas comparative examples are denoted by a letter.

EXAMPLES

Hair conditioning compositions were prepared having ingredients as shown in the following Table 1:

TABLE 1

| Trade name | Chemical name | Supplier | Example A | Example 1 |
|---|---|---|---|---|
| Genamin GDMP | Behentrimonium Chloride | Hoechst | 1.00 | 1.00 |
| Hydrenol MY | Cetearyl Alcohol | Cognis Thai | 3.5 | 3.5 |
| Stearyl Stearate | Stearyl Stearate | Croda | 1.00 | 1.00 |
| Paraffin wax | Paraffin wax | Shell | 1.00 | 1.00 |
| Climbazole | 1-(4-Chlorophenoxy)-1-(imidazolyl)-3,3-dimethyl-butanone | Yan Cheng Luye | 1.00 | 1.00 |
| Sunflower Oil | Sunflower Oil | Lam soon | — | 2.00 |

TABLE 1-continued

| Trade name | Chemical name | Supplier | Example A | Example 1 |
|---|---|---|---|---|
| DC-1785 | Dimethiconol | Dow Corning | 5.00 | 5.00 |
| Water | Chlorinated water | ULT | To 100% | To 100% |

The compositions were evaluated for the level of climbazole deposited on skin as follows:

Product Treatment

Artificial skin was snapped onto plastic cylinders prior to product treatment. Test shampoos were stirred and rubbed onto the artificial skin, at dilution of 1:3, using a wide diameter stirring rod for 30 seconds. Shampoo liquor was then removed from the artificial skin, followed by adequate rinsing with distilled water to remove any residual surfactants. Climbazole that was deposited from shampoo onto artificial skin was then extracted by ethanol. The ethanolic solution was then filtered through a 0.45 um filter to remove any impurities. Samples were analysed using HPLC.

The results of the evaluation are shown below in Table 2:

TABLE 2

|  | Climbazole deposition ($\mu g/cm^2$) |
|---|---|
| Example A | 8.37 |
| Example 1 | 27.33 |

Thus the example according to the invention deposited more climbazole onto the skin than the comparative example.

The invention claimed is:

1. A method of mitigating dandruff which method consisting of applying to the scalp:
   a hair conditioning composition consisting of behentrimonium chloride, cetearyl Alcohol, stearyl stearate, paraffin wax, climbazole, sunflower oil, dimethiconol and water.

* * * * *